United States Patent [19]

Bugaut et al.

[11] 4,149,848
[45] Apr. 17, 1979

[54] NOVEL PARA-PHENYLENEDIAMINE DYES FOR KERATIN FIBRES

[75] Inventors: Andrée Bugaut, Boulogne; Alain R. Genet, Neuilly Plaisance, both of France

[73] Assignee: L'Oreal, Paris, France

[21] Appl. No.: 912,977

[22] Filed: Jun. 5, 1978

[30] Foreign Application Priority Data

Jun. 24, 1977 [FR] France .................. 77 19530

[51] Int. Cl.$^2$ .................. D06P 1/32; A61K 7/13
[52] U.S. Cl. .................. 8/11; 8/10; 8/10.1; 8/10.2
[58] Field of Search .................. 8/10, 10.1, 10.2, 11

[56] References Cited

U.S. PATENT DOCUMENTS 2,364,350 12/1944 Dickey et al. .................. 96/66 HD
3,925,474 12/1975 Kalopissis et al. .................. 8/10

OTHER PUBLICATIONS

Corbett, "Hairdyes" in Venkataraman's The Chemistry of Synthetic Dyes, vol. V, (Academic Press, 1971), pp. 475-534.

Primary Examiner—A. Lionel Clingman
Attorney, Agent, or Firm—Brisebois & Kruger

[57] ABSTRACT

Compositions for dyeing keratin fibres are provided based on a novel para-phenylenediamine oxidative dye which has the formula:

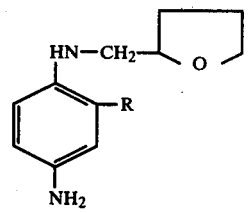

in which R represents hydrogen, chlorine or methyl or a salt thereof.

20 Claims, No Drawings

NOVEL PARA-PHENYLENEDIAMINE DYES FOR KERATIN FIBRES

This invention relates to dyeing compositions for keratin fibres.

It is known that, in dyeing compositions for keratin fibres, and especially for hair, when para-phenylenediamines are used they are generally associated with compounds which are commonly referred to as "couplers" or "toners". The para-phenylenediamines can, however, also be used by themselves in an alkaline oxidising medium or associated with other para-phenylenediamines. The association of couplers with para-phenylenediamines in an alkaline oxidising medium and, more particularly, in the presence of hydrogen peroxide, gives rise to the formation of indamines or indoanilines having very varied colours which depend on the nature of the coupler. It is clearly desirable that the para-phenylenediamines should be capable of imparting to the keratin fibres natural shades which have good stability to light, bad weather and washing.

The present invention provides new para-phenylenediamines for dyeing keratin fibres which satisfy the conditions indicated above very well. These para-phenylenediamines have the general formula:

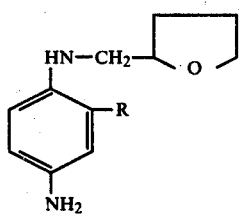

(I)

in which formula R represents a hydrogen atom, a chlorine atom or a methyl radical, as well as salts of these compounds, such as the hydrochlorides, sulphates, phosphates and tartrates.

The para-phenylenediamines of the general formula (I) may be prepared by reacting tetrahydrofurfurylamine with a halogen-containing derivative of the formula:

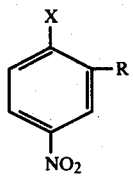

(II)

in which formula X represents a chlorine or fluorine atom and R represents a hydrogen or chlorine atom or a methyl radical. The substituted para-nitroanilines corresponding to the following general formula (III) lead, after reduction of their nitro group, to the para-phenylenediamines of the formula (I).

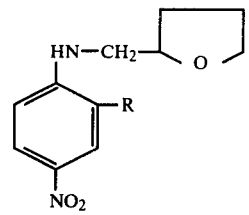

(III)

The present invention therefore provides a composition suitable for dyeing keratin fibres, and in particular human hair, the composition being characterised in that it contains, in aqueous solution, at least one compound of the formula (I) or a salt thereof.

It is generally necessary to add an oxidising agent, at the time of use, to the dyeing compositions according to the invention. The oxidising agent used is generally hydrogen peroxide, for example in an amount of 0.5 to 6% by weight; however, urea peroxide or a persalt such as ammonium persulphate can also be used.

When used by themselves in an alkaline oxidising medium, and preferably in the presence of ammoniacal hydrogen peroxide, the para-phenylenediamines of the formula (I) can impart to keratin fibres natural shades which have good stability to light, bad weather and washing.

The para-phenylenediamine of the formula (I) in which R represents hydrogen is particularly valuable for the dark colorations which it can impart to hair when used by itself in an alkaline oxidising medium. Depending on the concentration of the para-phenylenediamine, the nature of the carrier and the pH, it is generally possible to obtain black colorations for concentrations of 3 to 6% by weight, chestnut colorations for concentrations of 2 to 3% by weight and grey-beige colorations for lower concentrations. In certain carriers, the browns obtained can be more or less strongly shaded with violet. In all cases, the stability of these so-called "background" colorations is excellent.

When used by themselves in an alkaline oxidising medium, the para-phenylenediamines of the formula (I) in which R represents chlorine or a methyl radical impart to the hair golden or coppery colorations which have good resistance to light and bad weather, for example in humid atmospheres.

In the compositions of the present invention, the para-phenylenediamines of the formula (I) are generally associated with couplers. It is well-known that the association of couplers with para-phenylenediamines in an alkaline oxidising medium leads to the formation, in the keratin fibre, of indamines or indoanilines having very varied colours which depend on the nature of the coupler. These couplers can be; inter alia, (a) meta-phenylenediamines such as: 2,4-diaminoanisole, (2,4-diamino)-phenoxyethanol and 6-aminobenzomorpholine;

(b) meta-diphenols such as resorcinol, cresorcinol and chlororesorcinol;

(c) α-naphthol;

(d) meta-aminophenols such as meta-aminophenol, 2-methyl-5-aminophenol, 2,6-dimethyl-3-aminophenol, 2-methyl-5-(N-β-hydroxyethylamino)-phenol, 2-methyl-5-amino-6-nitrophenol, 2-methyl-5-(N-mesylaminoethylamino)-phenol and 6-hydroxybenzomorpholine (corresponding to the formula:

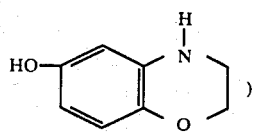

(e) meta-(acetylamino)-phenols such as 2,6-dimethyl-3-acetylaminophenol;
(f) meta-ureidophenols such as 2-methyl-5-ureidophenol;
(g) meta-(carbalkoxyamino)-phenols such as 2-methoxy-5-(carbethoxyamino)-phenol; and
(h) pyrazolones.

The shades obtained with a large number of these couplers are of good quality, that is to say that they only change slightly, if at all, in the light, in bad weather and on washing.

In particular, when it is associated with resorcinol, the para-phenylenediamine of the formula (I) in which R represents hydrogen imparts to the hair a golden beige of excellent stability. With meta-aminophenol, as ashen grey is obtained which is particularly valuable in formulation and exhibits very good resistance to strong light, bad weather and washing. The red-purple shade obtained with 2-methyl-5-(N-β-hydroxyethylamino)-phenol, the violet shade obtained with 2-methoxy-5-carbethoxyaminophenol and the bronzy green shade obtained with 6-hydroxybenzomorpholine are also of good quality. With (2,4-diamino)-phenoxyethanol, the para-phenylenediamine of the formula (I) in which R represents hydrogen imparts to the hair a slightly purplish blue shade which has good resistance to bad weather and washing but which, in strong light, loses the initial purple coloration to give a pure blue. With 6-aminobenzomorpholine, a pure blue is obtained which, in strong light, changes to a slightly greenish blue.

The dyeing compositions of this invention can contain, in addition to the oxidising bases of the formula (I); inter alia;
(a) other para-phenylenediamines such as para-phenylenediamine, 2,6-dimethyl-3-methoxy-para-phenylenediamine, 4-(N-ethyl-N-mesylaminoethylamino)-aniline, 4-(N,N-di-β-hydroxyethylamino)-aniline, 4-(N-ethyl-N-carbamylmethylamino)-aniline and 4-(N-β-methoxyethylamino)-aniline;
(b) ortho-phenylenediamines or ortho-aminophenols; and
(c) para-aminophenols such as para-aminophenol and 3-chloro-4-aminophenol.

The compositions of this invention can also contain leuco derivatives of indamines, of indoanilines or of indophenols, such as 4,4'-dihydroxy-5-aminomethyldiphenylamine and 2,4'-diamino-4-hydroxy-5-methyldiphenylamine. They can also contain nitro benzene dyestuffs, such as 3-nitro-4-(N-β-hydroxyethylamino)-phenol, 1-methoxy-3-nitro-6-(N-β-hydroxyethylamino)-benzene and 3-nitro-4-(N'-methylamino)-N-di-β-hydroxyethylaniline. They can also contain polyaminophenols, monoaminodiphenols, diaminodiphenols and polyphenols.

The concentration of the para-phenylenediamines of the formula (I) in the dyeing compositions according to the invention is generally 0.05 to 6% by weight, relative to the total weight of the composition.

The compositions are in the form of aqueous solutions to which there may be added, for example, one or more of the following: alkalising or acidifying agents, solvent, polymers, cationic treatment products, amides thickeners, surface-active agents or other additives which are usually employed in hair cosmetics, such as sunlight filters, optical brighteners, antioxidants, sequestering agents and perfumes.

The alkalising agents which may be used in the compositions of this invention include ammonia, mono- or tri-ethanolamine, sodium phosphate or carbonate, sodium hydroxide or potassium hydroxide; the acidifying agents can be phosphoric, hydrochloric, lactic, tartaric acetic or citric acid. They are intended for adjusting the pH of the dyeing composition to a value of, say, 8 to 11.5.

The solvents can be alcohols having 1 to 4 carbon atoms, such as ethyl alcohol or isopropyl alcohol, or glycols such as ethylene glycol, propylene glycol and the monobutyl, monoethyl and monomethyl ethers of ethylene glycol or of diethylene glycol. The abovementioned solvents are generally present in an amount of 0.5 to 50%, preferably 1 to 15%, by weight, relative to the total weight of the composition.

Suitable polymers are polymers or copolymers of vinylpyrrolidone, crotonic acid/vinyl acetate and vinylpyrrolidone/vinyl acetate copolymers, and cationic polymers such as wuaternised polymers of polyvinylpyrrolidone, quaternised derivatives of cellulose and copolymers of N-vinylpyrrolidone, dimethylaminoethyl methacrylate which has been quaternised with dimethyl sulphate, and polyethylene glycol, which polymders may or may not be crosslinked. The polymers are suitably introduced at concentrations of 0.1 to 3% by weight.

The amides which can be added include mono- or di-ethanolamides of optionally oxyethyleneated fatty acids.

The thickeners which can be added include cellulose derivatives such as carboxymethylcellulose, hydroxypropylmethylcellulose and hydroxyethylcellulose, sodium alginate, gum arabic, acrylic acid polymers and bentonite. Their concentration is generally 0.5 to 5% by weight, relative to the total weight of the composition.

The surface-active agents which can be added can be anionic, cationic, non-ionic or amphoteric, for example sulphates, ether-sulphates and sulphonates of fatty alcohols, optionally oxyethyleneated fatty acids or alcohols, oxyethyleneated alkylphenols, amines, and quaternised ammonium salts such as trimethylcetylammonium bromide and cetylpyridinium bromide. Their concentration is generally 0.5% to 30% by weight, relative to the total weight of the composition.

Benzylidene-camphor may be mentioned as an example of a sunlight filter; butylhydroxyanisole, sodium bisulphite and ascorbic acid may be mentioned as examples of antioxidants; ethylenediaminetetraacetic acid may be mentioned as an example of a complexing agent.

The dyeing compositions can be in the form of, for example, a gel, a cream, a foaming liquid or a milky liquid of variable viscosity and may be packaged in bottles, tubes or aerosol containers.

The compositions are suitably applied for 10 to 30 minutes, preferably 15 to 20 minutes.

The following Examples further illustrate the present invention including the preparation of the compounds of formula (I).

EXAMPLE 1

Preparation of 4-amino-N-tetrahydrofurfurylaniline dihydrochloride

This process comprises two stages which are shown by the following scheme:

1st Stage:

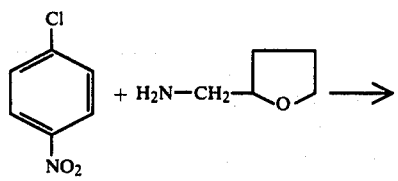

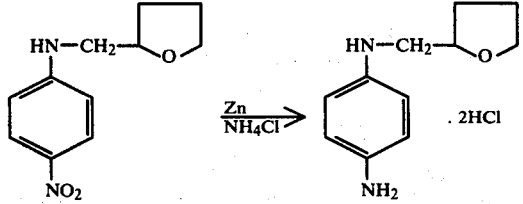

2nd Stage:

1st Stage: Preparation of 4-nitro-N-tetrahydrofurfurylaniline.

0.3 mol (46.2 g) of para-chloronitrobenzene and 1 mol (101 g) of tetrahydrofurfurylamine are heated for three hours in an oil bath at 150° C. The reaction medium is then poured into 500 ml of ice-cooled water. The expected product initially precipitates in the form of a thick oil which rapidly crystallises. After it has been filtered off, washed with water, recrystallised from ethanol and dried in vacuo, the product melts at 74° C.

Analysis of the product obtained gave the following results:

| Analysis | Calculated for $C_{11}H_{14}N_2O_3$ | Found |
|---|---|---|
| C% | 59.45 | 59.51 |
| H% | 6.35 | 6.45 |
| N | 12.60 | 12.57 |

2nd Stage: Preparation of 4-amino-N-tetrahydrofurfurylaniline dihydrochloride 4.02 g of ammonium chloride and 57 g of zinc powder are added to 180 ml of an aqueous-alcoholic solution (83% of alcohol and 17% of water). This mixture is heated to the reflux temperature, whilst stirring, and 0.122 mol (27 g) of 4-nitro-N-tetrahydrofurfurylaniline is then added gradually. When the reaction medium is decolorised, it is filtered and the filtrate is collected in a flask containing 30 ml of ice-cooled hydrochloric acid (d=1.19). On cooling, the expected dihydrochloride precipitates in the form of crystals. It is filtered off and washed with absolute alcohol and then acetone. After drying in vacuo, it melts at about 190° C. with decomposition.

Analysis of the product obtained gave the following results:

| Analysis | Calculated for $C_{11}H_{16}N_2O \cdot 2HCl$ | Found |
|---|---|---|
| C % | 49.82 | 49.83 |
| H % | 6.84 | 7.03 |
| N % | 10.56 | 10.68 |
| Cl % | 26.74 | 26.60 |

EXAMPLE 2

Preparation of 2-methyl-4-amino-N-tetrahydrofurfurylaniline dihydrochloride monohydrate.

This process comprises two stages which are shown by the following equations:

1st Stage:

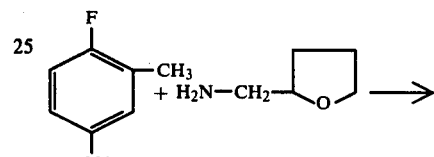

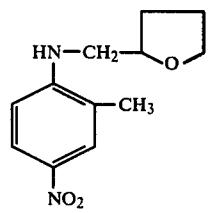

2nd Stage:

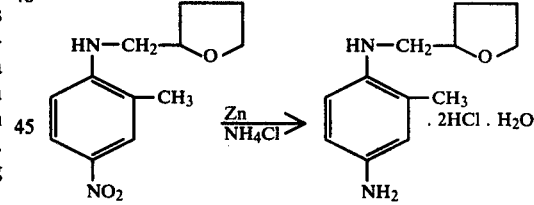

1st Stage: Preparation of 2-methyl-4-nitro-N-tetrahydrofurfurylaniline

A mixture of 0.2 mol (31.0 g) of 3-methyl-4-fluoronitrobenzene and 0.7 mol (70.7 g) of tetrahydrofurfurylamine is heated for one hour in an oil bath at 140° C. The reaction mixture is then poured into 400 g of ice-cooled water. The expected product rapidly crystallises; after it has been filtered off, washed with water, recrystallised from ethanol and dried in vacuo, it melts at 60° C.

Analysis of the product obtained gave the following results:

| Analysis | Calculated for $C_{12}H_{16}N_2O_3$ | Found |
|---|---|---|
| C % | 61.00 | 61.06 |
| H % | 6.83 | 6.76 |
| N % | 11.86 | 11.73 |

2nd Stage: Preparation of 2-methyl-4-amino-N-tetrahydrofurfurylaniline dihydrochloride monohydrate 5 g of ammonium chloride and 83 g of zinc powder are added to 250 ml of an aqueous-alcoholic solution (85% of alcohol and 15% of water). This mixture is heated to the reflux temperature, whilst stirring, and 0.168 mol (39.8 g) of 2-methyl-4-nitro-N-tetrahydrofurfurylaniline is then added gradually. When the addition of the nitro derivative has ended and the reaction medium is completely decolorised, the latter is filtered and the filtrate is collected in 40 ml of ice-cooled hydrochloric acid (d=1.19). 80 ml of acetone are added to the filtrate. 2-Methyl-4-amino-N-tetrahydrofurfurylaniline dihydrochloride precipitates in the form of the monohydrate. The crystalline product is filtered off and washed with absolute alcohol and then acetone. After drying in vacuo, it melts at about 210° C. with decomposition.

Analysis of the product obtained gave the following results:

| Analysis | Calculated for $C_{12}H_{18}N_2O \cdot 2HCl \cdot H_2O$ | Found |
|---|---|---|
| C % | 48.50 | 48.76 |
| H % | 7.46 | 7.57 |
| N % | 9.43 | 9.24 |
| Cl % | 23.86 | 23.75 |

EXAMPLE 3

Preparation of 2-chloro-4-amino-N-tetrahydrofurfurylaniline monohydrochloride This process comprises two stages which are shown by the following equations:

1st Stage:

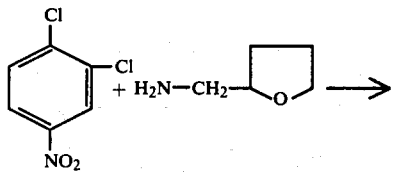

2nd Stage:

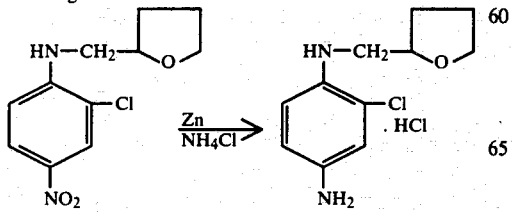

1st Stage: Preparation of 2-chloro-4-nitro-N-tetrahydrofurfurylaniline

A mixture of 0.3 mol (57.6 g) of 3,4-dichloronitrobenzene and 1 mol (101 g) of tetrahydrofurfurylamine is heated in an oil bath. When the temperature of the reaction medium reaches 110° C., the reaction starts and the temperature rises rapidly to 160° C. and is maintained for a certain time without external heating. When the temperature falls, the reaction medium is heated for 30 minutes in an oil bath at 150° C. and is then poured into 500 ml of ice-cooled water. The expected product initially precipitates in the form of an oil which rapidly crystallises. After it has been filtered off, washed with water, recrystallised and dried in vacuo, the product melts at 70° C.

Analysis of the product obtained gave the following results:

| Analysis | Calculated for $C_{11}H_{13}ClN_2O_3$ | Found |
|---|---|---|
| C % | 51.47 | 51.34 |
| H % | 5.10 | 5.30 |
| N % | 10.91 | 10.94 |
| Cl % | 13.81 | 13.68 |

2nd Stage: Preparation of 2-chloro-4-amino-N-tetrahydrofurfurylaniline monohydrochloride 3.0 g of ammonium chloride and 50 g of zinc powder are added to 150 ml of an aqueous-alcoholic solution (85% of alcohol and 15% of water). This mixture is heated to the reflux temperature, whilst stirring, and 0.1 mol (25.7 g) of 2-chloro-4-nitro-N-tetrahydrofurfurylaniline is then added gradually. When the addition has ended and the reaction mixture is decolorised, the latter is filtered and the filtrate is collected in 20 ml of ice-cooled hydrochloric acid. After cooling, the expected hydrochloride precipitates in the form of crystals. It is filtered off, washed with a small amount of ice-cooled absolute alcohol and dried in vacuo. It melts at about 170° C. with decomposition.

Analysis of the product obtained gave the following results:

| Analysis | Calculated for $C_{11}H_{15}N_2OCl \cdot HCl$ | Found |
|---|---|---|
| C % | 50.20 | 50.20 |
| H % | 6.13 | 6.38 |
| N % | 10.64 | 10.76 |
| Cl % | 26.95 | 26.94 |

EXAMPLE 4

The following dyeing composition is prepared:

| | |
|---|---|
| Compound of Example 1 | 2.12 g |
| 96° strength alcohol | 17.8 g |
| Sodium sulphite | 0.1 g |
| Triethanolamine | 8.0 g |
| Water q.s.p. | 100 g |
| The pH of this composition is equal to 8.5. | |

100 g of hydrogen peroxide of 20 volumes strength are added at the time of use. When applied to bleached hair for 30 minutes at 25° C., this mixture imparts to the hair, after rinsing and shampooing, a deep brown coloration with a purple-violet sheen.

EXAMPLE 5

The following dyeing composition is prepared:

| | |
|---|---|
| Compound of Example 1 | 1.33 g |
| Propylene glycol | 10 g |
| Diethanolamides of copra fatty acids | 5 g |
| 22° B strength ammonia solution | 10 g |
| Water q.s.p. | 100 g |
| The pH of this composition is equal to 10.4 | |

100 g of hydrogen peroxide of 20 volumes strength are added at the time of use. When applied to bleached hair for 20 minutes at 27° C., this mixture imparts to the hair, after rinsing and shampooing, an ashen beige grey coloration.

EXAMPLE 6

The following dyeing composition is prepared:

| | |
|---|---|
| Compound of Example 1 | 6 g |
| Carboxymethylcellulose | 1.9 g |
| Ammonium lauryl-sulphate | 4.7 g |
| Ammonium acetate | 0.94 g |
| Propylene glycol | 7.52 g |
| 22° B strength ammonia solution | 11.4 g |
| Water q.s.p. | 100 g |
| The pH of this composition is equal to 9.2 | |

100 grams of hydrogen peroxide of 20 volumes strength are added at the time of use. When applied to bleached hair for 20 minutes at 27° C., this mixture imparts to the hair, after rinsing and shampooing, an anthracite black coloration.

EXAMPLE 7

The following dyeing composition is prepared:

| | |
|---|---|
| Compound of Example 1 | 2.65 g |
| Sodium salt of the sulphate half-ester of lauryl alcohol oxyethyleneated with 2 mols of ethylene oxide, containing 19% of starting oxyethyleneated lauryl alcohol | 20 g |
| Ethylenediaminetetraacetic acid | 0.2 g |
| 40% Strength aqueous sodium bisulphite solution | 1 g |
| 22° B strength ammonia solution | 10 g |
| Water q.s.p. | 100 g |
| The pH of this composition is equal to 10. | |

100 g of hydrogen peroxide of 20 volumes strength are added at the time of use. When applied at 95% strength to natural white hair for 20 minutes at 25° C., the mixture imparts to the hair, after rinsing and shampooing, a deep chestnut coloration.

EXAMPLE 8

The following dyeing composition is prepared:

| | |
|---|---|
| Compound of Example 1 | 6 g |
| Ortho-aminophenol | 0.88 g |
| Carboxymethylcellulose | 1.9 g |
| Ammonium lauryl-sulphate | 4.7 g |
| Ammonium acetate | 0.9 g |
| Propylene glycol | 7.4 g |
| 22° B strength ammonia solution | 11.2 g |
| Water q.s.p. | 100 g |
| The pH of this composition is equal to 9.1. | |

100 g of hydrogen peroxide of 20 volumes strength are added at the time of use. When applied at 95% strength to natural white hair for 20 minutes at 27° C., the mixture imparts a jet black coloration to the hair.

EXAMPLE 9

The following dyeing composition is prepared:

| | |
|---|---|
| Compound of Example 1 | 1.33 g |
| 2,6-Dimethyl-3-acetylaminophenol | 0.89 g |
| Ammonium $C_{12},C_{14}$-alkyl-sulphate (70% of $C_{12}$ and 30% of $C_{14}$) | 14.7 g |
| Lauryl alcohol oxyethyleneated with 10.5 mols of ethylene oxide | 4.9 g |
| 22° B strength ammonia solution | 9.8 g |
| Water q.s.p. | 100 g |
| The pH of this composition is equal to 10.2. | |

100 g of hydrogen peroxide of 20 volumes strength are added at the time of use. When applied to bleached hair for 20 minutes at 27° C., this mixture imparts to the hair, after rinsing and shampooing, an intense royal blue shade.

EXAMPLE 10

The following dyeing composition is prepared:

| | |
|---|---|
| Compound of Example 1 | 0.66 g |
| 6-Hydroxybenzomorpholine | 0.377 g |
| Sodium salt of the sulfate half-ester of lauryl alcohol oxyethyleneated with 2 mols of ethylene oxide, containing 19% of starting oxyethyleneated lauryl alcohol | 20 g |
| Ethylenediaminetetraacetic acid | 0.2 g |
| 40% Strength sodium bisulphite solution | 1 g |
| 22° B strength ammonia solution | 10 g |
| Water q.s.p. | 100 g |
| The pH of this composition is equal to 10.5. | |

90 g of hydrogen peroxide of 20 volumes strength are added at the time of use. When applied at 95% strength to natural white hair for 20 minutes at 25° C., this mixture imparts to the hair, after rinsing and shampooing, a bronzy green coloration.

EXAMPLE 11

The following dyeing composition is prepared:

| | |
|---|---|
| Compound of Example 1 | 0.66 g |
| Meta-aminophenol | 0.272 g |
| Sodium salt of the sulphate half-ester of lauryl alcohol oxyethyleneated with 2 mols of ethylene oxide, containing 19% of starting oxyethyleneated lauryl alcohol | 20 g |
| Ethylenediaminetetraacetic acid | 0.2 g |
| Aqueous sodium bisulphite solution (40% strength) | 1 g |
| 22° B strength ammonia solution | 10 g |
| Water q.s.p. | 100 g |
| The pH is equal to 10.5. | |

100 g of hydrogen peroxide of 20 volumes strength are added at the time of use. When applied at 95% strength to natural white hair for 20 minutes at 25° C., this mixture imparts to the hair, after rinsing and shampooing, an ashen grey coloration.

EXAMPLE 12

The following dyeing composition is prepared:

| | |
|---|---|
| Compound of Example 1 | 0.66 g |
| (2,4-Diamino)-phenoxyethanol dihydrochloride | 0.602 g |
| Sodium salt of the sulphate half-ester of lauryl alcohol oxyethyleneated with 2 mols of ethylene | |

-continued

| | |
|---|---|
| oxide, containing 19% of starting oxyethyleneated lauryl alcohol | 20 g |
| Ethylenediaminetetraacetic acid | 0.2 g |
| Aqueous sodium bisulphite solution (40% strength) | 1 g |
| 22° B strength ammonia solution | 10 g |
| Water q.s.p. | 100 g |
| The pH of this composition is equal to 10.5. | |

100 g of hydrogen peroxide of 20 volumes strength are added at the time of use. When applied at 95% strength to natural white hair for 20 minutes at 25° C., this mixture imparts to the hair, after rinsing and shampooing, a fairly dark pure blue coloration.

EXAMPLE 13

The following dyeing composition is prepared:

| | |
|---|---|
| Compound of Example 1 | 3.98 g |
| 6-Aminobenzomorpholine dihydrochloride | 1.67 g |
| Ammonium $C_{12}$, $C_{14}$-alkyl-sulphate (70% bf $C_{12}$ and 30% 0f $C_{14}$) | 14.7 g |
| Lauryl alcohol containing 10.5 mols of ethylene oxide (i.e. oxyethyleneated) | 4.7 g |
| 22° B strength ammonia solution | 9.5 g |
| Water q.s.p. | 100 g |
| The pH of this composition is equal to 9.4. | |

100 g of hydrogen peroxide of 20 volumes strength are added at the time of use. When applied to bleached hair for 15 minutes at 30° C., this mixture imparts to the hair, after rinsing and shampooing, a fairly dark pure blue coloration.

EXAMPLE 14

The following dyeing composition is prepared:

| | |
|---|---|
| Compound of Example 1 | 0.66 g |
| 2,6-Dimethyl-3-aminophenol | 0.342 g |
| Sodium salt of the sulphate half-ester of lauryl alcohol oxyethyleneated with 2 mols of ethylene oxide, containing 19% of starting oxyethyleneated lauryl alcohol | 20 g |
| Ethylenediaminetetraacetic acid | 0.2 g |
| Aqueous sodium bisulphite solution (40% strength) | 1 g |
| 22° B strength ammonia solution | 10 g |
| Water q.s.p. | 100 g |
| The pH of this composition is equal to 10.5. | |

100 g of hydrogen peroxide of 20 volumes strength are added at the time of use. When applied at 95% strength to natural white hair for 20 minutes at 25° C., this mixture imparts to the hair, after rinsing and shampooing, a purple shade.

EXAMPLE 15

The following dyeing composition is prepared:

| | |
|---|---|
| Compound of Example 1 | 0.75 g |
| 2-Methyl-5-(N-$\beta$-hydroxyethylamino)-phenol | 0.47 g |
| Ammonium $C_{12}$, $C_{14}$-alkyl-sulphate (70% of $C_{12}$ and 30% of $C_{14}$) | 14.8 g |
| Lauryl alcohol containing 10.5 mols of ethylene oxide | 4.95 g |
| 22° B strength ammonia solution | 9.9 g |
| Water q.s.p. | 100 g |
| The pH of this composition is equal to 10.3. | |

100 g of hydrogen peroxide of 20 volumes strength are added at the time of use. When applied to bleached hair for 20 minutes at 27° C., this mixture imparts to the hair, after rinsing and shampooing, a cyclamen coloration.

EXAMPLE 16

The following dyeing composition is prepared:

| | |
|---|---|
| Compound of Example 1 | 0.3 g |
| Para-aminophenol | 0.03 g |
| 2-Methyl-5-(N-$\beta$-hydroxyethylamino)-phenol | 0.06 g |
| 2,6-Dimethyl-3-acetylaminophenol | 0.155 g |
| Ethylene glycol monobutyl ether | 4.75 g |
| Lauryl alcohol oxyethyleneated with 10.5 mols of ethylene oxide | 4.75 g |
| 22° B strength ammonia solution | 10 g |
| Water q.s.p. | 100 g |
| The pH of this composition is equal to 10.9. | |

100 g of hydrogen peroxide of 20 volumes strength are added at the time of use. When applied to bleached hair for 20 minutes at 25° C., this mixture imparts to the hair, after rinsing and shampooing, a dove grey coloration.

EXAMPLE 17

The following dyeing composition is prepared:

| | |
|---|---|
| Compound of Example 1 | 1 g |
| 6-Hydroxybenzomorpholine | 0.05 g |
| 2-Methyl-5-carbethoxyaminophenol | 0.2 g |
| 2-Hydroxy-1,4-naphthoquinone | 2 g |
| Ethylene glycol monobutyl ether | 20 g |
| Ammonium lauryl-sulphate | 7 g |
| Triethanolamine | 8 g |
| Water q.s.p. | 100 g |
| The pH of this composition is equal to 8.5. | |

30 g of hydrogen peroxide of 20 volumes strength are added at the time of use. When applied to bleached hair for 20 minutes at 26° C., this mixture imparts to the hair, after rinsing and shampooing, a very golden sand coloration.

EXAMPLE 18

The following dyeing composition is prepared:

| | |
|---|---|
| Compound of Example 1 | 5.3 g |
| 2-Methyl-5-amino-6-nitrophenol | 1.7 g |
| 2,6-Dimethyl-3-nitro-4-(N-$\beta$-hydroxyethylamino)-phenol | 1.5 g |
| Carboxymethylcellulose | 4.45 g |
| Ethylene glycol monobutyl ether | 13 g |
| 22° B strength ammonia solution | 10 g |
| Water q.s.p. | 100 g |
| The pH of this composition is equal to 8.5. | |

90 g of hydrogen peroxide of 20 volumes strength are added at the time of use. When applied to bleached hair for 20 minutes at 24° C., this mixture imparts to the hair, after rinsing and shampooing, a blackish blue coloration.

EXAMPLE 19

The following dyeing composition is prepared:

| | |
|---|---|
| Compound of Example 1 | 5.3 g |
| Ortho-aminophenol | 0.55 g |
| 2,6-Dimethyl-3-acetylaminophenol | 0.89 g |
| Ammonium $C_{12}$, $C_{14}$-alkyl-sulphate (70% 0f $C_{12}$ and 30% of $C_{14}$) | 14.10 g |
| Lauryl alcohol containing 10 mols of ethylene oxide | 4.7 g |

-continued

| | |
|---|---|
| 22° B strength ammonia solution | 9.4 g |
| Water q.s.p. | 100 g |
| The pH of this composition is equal to 9.3. | |

100 g of hydrogen peroxide of 20 volumes strength are added at the time of use. When applied to bleached hair for 20 minutes at 27° C., this mixture imparts to the hair, after rinsing and shampooing, a raven black coloration.

EXAMPLE 20

The following dyeing composition is prepared:

| | |
|---|---|
| Compound of Example 1 | 0.5 g |
| Para-aminophenol | 0.8 g |
| α-Naphthol | 0.3 g |
| Resorcinol | 0.4 g |
| 6-Hydroxybenzomorpholine | 0.04 g |
| Nitro-para-phenylenediamine | 0.03 g |
| Ortho-aminophenol | 0.15 g |
| Ethylene glycol monobutyl ether | 4.9 g |
| Lauryl alcohol oxyethyleneated with 10.5 mols of ethylene oxide | 4.9 g |
| 22° B strength ammonia solution | 9.8 g |
| Water q.s.p. | 100 g |
| The pH of this composition is equal to 10.4. | |

80 g of hydrogen peroxide of 20 volumes strength are added at the time of use. When applied to bleached hair for 20 minutes at 23° C., this mixture imparts to the hair, after rinsing and shampooing, a copper-red deep chestnut coloration.

EXAMPLE 21

The following dyeing composition is prepared:

| | |
|---|---|
| Compound of Example 1 | 0.743 g |
| 2,6-Dimethyl-3-aminophenol | 0.096 g |
| Ortho-aminophenol | 0.218 g |
| Propylene glycol | 10 g |
| 22° B strength ammonia solution | 10 g |
| Diethanolamides of copra fatty acids | 5 g |
| Water q.s.p. | 100 g |
| The pH of this composition is equal to 10.4. | |

90 g of hydrogen peroxide of 20 volumes strength are added at the time of use. When applied to bleached hair for 20 minutes at 27° C., this mixture imparts to the hair, after rinsing and shampooing, a deep beige coloration with a slight pink sheen.

EXAMPLE 22

The following dyeing composition is prepared:

| | |
|---|---|
| Compound of Example 1 | 0.1 g |
| Para-aminophenol | 0.08 g |
| 4-(N,N-Di-β-hydroxyethylamino)-aniline sulphate | 0.10 g |
| 2-Methyl-5-(N-β-hydroxyethylamino)-phenol | 0.15 g |
| Ethylene glycol monobutyl ether | 10 g |
| Carboxymethylcellulose | 3.5 g |
| Triethanolamine | 5 g |
| Water q.s.p. | 100 g |
| The pH of this composition is equal to 8.5. | |

20 g of hydrogen peroxide of 20 volumes strength are added at the time of use. When applied to bleached hair for 20 minutes at 25° C., this mixture imparts to the hair, after rinsing and shampooing, a pinkish raw silk coloration.

EXAMPLE 23

The following dyeing composition is prepared:

| | |
|---|---|
| Compound of Example 1 | 1.5 g |
| 4-(N-Ethyl-N-mesylaminoethylamino)-aniline sulphate | 2.0 g |
| Para-aminophenol | 0.5 g |
| 4-(N-Methylamino)-phenol sulphate | 0.2 g |
| Meta-aminophenol | 1.0 g |
| Resorcinol | 0.3 g |
| (2,4-Diamino)-phenoxyethanol dihydrochloride | 0.2 g |
| Ortho-aminophenol | 0.1 g |
| 3-Nitro-4-(N-β-hydroxyethylamino)-phenol | 0.09 g |
| Ethylene glycol monobutyl ether | 15 g |
| Nonylphenol oxyethyleneated with 4 mols of ethylene oxide | 13 g |
| Nonylphenol oxyethyleneated with 9 mols of ethylene oxide | 13 g |
| 22° B strength ammonia solution | 10 g |
| Water q.s.p. | 100 g |
| The pH of this composition is equal to 10. | |

70 g of hydrogen peroxide of 20 volumes strength are added at the time of use. When applied to bleached hair for 20 minutes at 20° C., this mixture imparts to the hair, after rinsing and shampooing, a very dark smoke-grey coloration.

EXAMPLE 24

The following dyeing composition is prepared:

| | |
|---|---|
| Compound of Example 1 | 0.133 g |
| Para-phenylenediamine dihydrochloride | 0.94 g |
| Para-aminophenol | 1 g |
| 6-Hydroxybenzomorpholine | 0.4 g |
| 2-Methyl-5-amino-6-nitrophenol | 1.5 g |
| Carboxymethylcellulose | 2 g |
| Ammonium lauryl-sulphate | 5 g |
| Ammonium acetate | 1 g |
| Propylene glycol | 8 g |
| 22° B strength ammonia solution | 12 g |
| Water q.s.p. | 100 g |
| The pH of this composition is equal to 9.9. | |

100 g of hydrogen peroxide of 20 volumes strength are added at the time of use. When applied to bleached hair for 20 minutes at 27° C., this mixture imparts to the hair, after rinsing and shampooing, a copper-red chestnut coloration.

EXAMPLE 25

The following dyeing composition is prepared:

| | |
|---|---|
| Compound of Example 1 | 0.3 g |
| Para-aminophenol | 0.6 g |
| α-Naphthol | 0.42 g |
| Resorcinol | 0.4 g |
| 2-Methyl-5-(N-β-hydroxyethylamino)-phenol | 0.2 g |
| Ethylene glycol monobutyl ether | 15 g |
| Acrylic acid polymer (molecular weight = 2 to 3,000,000) sold by the Company called "Goodrich Chemical Co." under the name "Carbopol 934" | 3.3 g |
| 22° B strength ammonia solution | 10 g |
| Water q.s.p. | 100 g |
| The pH of this composition is equal to 10.5. | |

50 g of hydrogen peroxide of 20 volumes strength are added at the time of use. When applied to bleached hair for 20 minutes at 27° C., this mixture imparts to the hair, after rinsing and shampooing, a rosewood coloration.

EXAMPLE 26

The following dyeing composition is prepared:

| | | |
|---|---|---|
| Compound of Example 1 | 0.5 | g |
| Para-aminophenol | 0.8 | g |
| Resorcinol | 0.3 | g |
| α-Naphthol | 0.3 | g |
| 6-Hydroxybenzomorpholine | 0.04 | g |
| Ortho-aminophenol | 0.15 | g |
| 2,6-Dimethyl-3-nitro-4-(N-β-hydroxyethylamino)-phenol | 0.03 | g |
| Oleyl alcohol oxyethyleneated with 2 mols of ethylene oxide | 4.4 | g |
| Oleyl alcohol oxyethyleneated with 4 mols of ethylene oxide | 4.4 | g |
| Oleylamine oxyethyleneated with 2 mols of ethylene oxide | 4.4 | g |
| Diethanolamides of copra fatty acids | 8.7 | g |
| Propylene glycol | 3.5 | g |
| Ethylene glycol monobutyl ether | 7.8 | g |
| Ethanol | 5.2 | g |
| Aqueous sodium bisulphite solution (d = 1.32) | 0.87 | g |
| 22° B strength ammonia solution | 9.7 | g |
| Water q.s.p. | 100 | g |
| The pH of this composition is equal to 9.5. | | |

100 g of hydrogen peroxide of 20 volumes strength are added at the time of use. When applied to bleached hair for 20 minutes at 26° C., this mixture imparts to the hair, after rinsing and shampooing, a golden light chestnut coloration.

EXAMPLE 27

The following dyeing composition is prepared:

| | | |
|---|---|---|
| Compound of Example 1 | 0.04 | g |
| (2,4-Diamino)-phenoxyethanol dihydrochloride | 0.009 | g |
| 2,6-Dimethyl-3-aminophenol hydrochloride | 0.007 | g |
| Ammonium lauryl-sulphate | 8.7 | g |
| 22° B strength ammonium solution | 3 | g |
| Water q.s.p. | 100 | g |
| The pH of this composition is equal to 10. | | |

10 g of hydrogen peroxide of 20 volumes strength are added at the time of use. When applied to bleached hair for 30 minutes at 25° C., this mixture imparts to the hair, after rinsing and shampooing, a pearlescent light blond coloration.

EXAMPLE 28

The following dyeing composition is prepared:

| | | |
|---|---|---|
| Compound of Example 1 | 0.4 | g |
| 2,6-Dimethyl-3-methoxy-para-phenylenediamine dihydrochloride | 0.17 | g |
| 6-Aminobenzomorpholine dihydrochloride | 0.06 | g |
| 2,6-Dimethyl-3-aminophenol hydrochloride | 0.06 | g |
| 2,6-Dimethyl-3-nitro-4-(N-β-hydroxyethylamino)-phenol | 0.05 | g |
| 6-Hydroxybenzomorpholine | 0.07 | g |
| Diethylene glycol monomethyl ether | 9 | g |
| 22° B strength ammonia solution | 10 | g |
| Water q.s.p. | 100 | g |
| The pH of this composition is equal to 11. | | |

100 g of hydrogen peroxide of 20 volumes strength are added at the time of use. When applied at 95% strength to natural white hair for 20 minutes at 20° C., this mixture imparts to the hair, after rinsing and shampooing, a silvery grey coloration with a mauve shade.

EXAMPLE 29

The following dyeing composition is prepared:

| | | |
|---|---|---|
| Compound of Example 2 | 1.39 | g |
| Propylene glycol | 10 | g |
| Diethanolamides of copra fatty acids | 5 | g |
| 22° B strength ammonia solution | 10 | g |
| Water q.s.p. | 100 | g |
| The pH of this composition is equal to 10.4. | | |

90 g of hydrogen peroxide of 20 volumes strength are added at the time of use. When applied to bleached hair for 20 minutes at 30° C., this mixture imparts to the hair, after rinsing and shampooing, a golden sand coloration.

EXAMPLE 30

The following dyeing composition is prepared:

| | | |
|---|---|---|
| Compound of Example 2 | 2.5 | g |
| Meta-aminophenol | 0.3 | g |
| Resorcinol | 0.3 | g |
| 1-(N,N-Di-β-hydroxyethylamino)-3-nitro-4-(N'-methylamino)-benzene | 3.6 | g |
| Propylene glycol | 9.3 | g |
| Diethanolamides of copra fatty acids | 4.6 | g |
| 22° B strength ammonia solution | 9.3 | g |
| Water q.s.p. | 100 | g |
| The pH of this composition is equal to 10. | | |

100 g of hydrogen peroxide of 20 volumes strength are added at the time of use. When applied to bleached hair for 20 minutes at ambient temperature, this mixture imparts to the hair, after rinsing and shampooing, a dark grey coloration with a violet shade.

EXAMPLE 31

The following dyeing composition is prepared:

| | | |
|---|---|---|
| Compound of Example 2 | 0.25 | g |
| 4-(N-Ethyl-N-mesylaminoethylamino)-aniline sulphate | 0.1 | g |
| α-Naphthol | 0.09 | g |
| 2-Methyl-5-(N-β-hydroxyethylamino)-phenol | 0.05 | g |
| 3-Nitro-4-(N-methylamino)-phenoxyethanol | 0.15 | g |
| Oleyl alcohol oxyethyleneated with 2 mols of ethylene oxide | 4.5 | g |
| Oleyl alcohol oxyethyleneated with 4 mols of ethylene oxide | 4.5 | g |
| Oleylamine oxyethyleneated with 2 mols of ethylene oxide | 4.5 | g |
| Diethanolamides of copra fatty acids | 9 | g |
| Propylene glycol | 3.6 | g |
| Ethylene glycol monobutyl ether | 8 | g |
| Ethanol | 5.4 | g |
| Aqueous sodium bisulphite solution (d = 1.32) | 1 | g |
| 22° B strength ammonia solution | 10 | g |
| Water q.s.p. | 100 | g |
| The pH of this composition is equal to 10. | | |

50 g of hydrogen peroxide of 20 volumes strength are added at the time of use. When applied to bleached hair for 15 minutes at 26° C., this mixture imparts to the hair, after rinsing and shampooing, a pinkish beige coloration.

EXAMPLE 32

The following dyeing composition is prepared:

| | | |
|---|---|---|
| Compound of Example 2 | 0.3 | g |
| Para-aminophenol | 0.4 | g |
| Resorcinol | 0.1 | g |
| 2,6-Dimethyl-3-acetylaminophenol | 0.2 | g |
| 6-Hydroxybenzomorpholine | 0.03 | g |
| 2,6-Dimethyl-3-nitro-4-(N-β-hydroxyethylamino)-phenol | 0.015 | g |
| Ethylene glycol monobutyl ether | 15 | g |

| | | |
|---|---|---|
| Diethanolamides of copra fatty acids | 7.8 | g |
| 22° B strength ammonia solution | 8 | g |
| Water q.s.p. | 100 | g |
| The pH of this composition is equal to 11. | | |

20 g of hydrogen peroxide of 20 volumes strength are added at the time of use. When applied to bleached hair for 20 minutes at 26° C., this mixture imparts to the hair, after rinsing and shampooing, a coppery blond coloration.

EXAMPLE 33

The following dyeing composition is prepared:

| | | |
|---|---|---|
| Compound of Example 2 | 0.4 | g |
| Para-aminophenol | 0.3 | g |
| Resorcinol | 0.1 | g |
| 2,6-Dimethyl-5-acetylaminophenol | 0.214 | g |
| 6-Aminobenzomorpholine dihydrochloride | 0.16 | g |
| 6-Hydroxybenzomorpholine | 0.1 | g |
| 2,6-Dimethyl-3-nitro-4-(β-hydroxyethylamino)-phenol | 0.03 | g |
| Ethylene glycol monobutyl ether | 15 | g |
| Nonylphenol oxyethyleneated with 4 mols of ethylene oxide | 15 | g |
| Nonylphenol oxyethyleneated with 9 mols of ethylene oxide | 15 | g |
| Triethanolamine | 8 | g |
| Water q.s.p. | 100 | g |
| The pH of this composition is equal to 9.1. | | |

30 g of hydrogen peroxide of 20 volumes strength are added at the time of use. When applied to bleached hair for 20 minutes at 26° C., this mixture imparts to the hair, after rinsing and shampooing, a grey-beige coloration.

EXAMPLE 34

The following dyeing composition is prepared:

| | | |
|---|---|---|
| Compound of Example 2 | 4 | g |
| 4-(N-Ethyl-N-β-mesylaminoethylamino)-aniline sulphate | 5.2 | g |
| Para-aminophenol | 1 | g |
| Resorcinol | 0.5 | g |
| α-Naphthol | 2 | g |
| Oleyl alcohol oxyethyleneated with 2 mols of ethylene oxide | 3.9 | g |
| Oleyl alcohol oxyethyleneated with 4 mols of ethylene oxide | 3.9 | g |
| Oleylamine oxyethyleneated with 2 mols of ethylene oxide | 3.9 | g |
| Diethanolamides of copra fatty acids | 7.8 | g |
| Propylene glycol | 3.1 | g |
| Ethylene glycol monobutyl ether | 7 | g |
| Ethanol | 4.7 | g |
| Aqueous sodium bisulphite solution (d = 1.32) | 1 | g |
| 22° B strength ammonia solution | 10 | g |
| Water q.s.p. | 100 | g |
| The pH of this composition is equal to 9.3. | | |

100 g of hydrogen peroxide of 20 volumes strength are added at the time of use. When applied to bleached hair for 25 minutes at 24° C., this mixture imparts to the hair, after rinsing and shampooing, a black coloration with a purplish-blue sheen.

EXAMPLE 35

The following dyeing composition is prepared:

| | | |
|---|---|---|
| Compound of Example 3 | 2.1 | g |
| Oleyl alcohol oxyethyleneated with 2 mols of ethylene oxide | 4.5 | g |
| Oleyl alcohol oxyethyleneated with 4 mols of ethylene oxide | 4.5 | g |
| Laurylamine oxyethyleneated with 12 mols of ethylene oxide | 4.5 | g |
| Diethanolamides of copra fatty acids | 9 | g |
| Propylene glycol | 3.6 | g |
| Ethylene glycol monobutyl ether | 8 | g |
| Ethanol | 5.4 | g |
| Aqueous sodium bisulphite solution (40% strength) | 1 | g |
| 22° B strength ammonia solution | 10 | g |
| Water q.s.p. | 100 | g |
| The pH of this composition is equal to 10. | | |

100 g of hydrogen peroxide of 20 volumes strength are added at the time of use. When applied to bleached hair for 25 minutes at 25° C., this mixture imparts to the hair, after rinsing and shampooing, a light copper coloration.

EXAMPLE 36

The following dyeing composition is prepared:

| | | |
|---|---|---|
| Compound of Example 3 | 0.657 | g |
| (2,4-Diamino)-phenoxyethanol dihydrochloride | 0.602 | g |
| Ammonium $C_{12}$, $C_{14}$-alkyl-sulphate (70% of $C_{12}$ and 30% of $C_{14}$) | 15 | g |
| Lauryl alcohol containing 10.5 mols of ethylene oxide | 5 | g |
| 22° B strength ammonia solution | 10 | g |
| Water q.s.p. | 100 | g |
| The pH of this composition is equal to 10.5. | | |

50 g of hydrogen peroxide of 20 volumes strength are added at the time of use. When applied at 95% strength to natural white hair for 30 minutes at 30° C., this mixture imparts to the hair, after rinsing and shampooing, a silvery light grey coloration with a bluish sheen.

EXAMPLE 37

The following dyeing composition is prepared:

| | | |
|---|---|---|
| Compound of Example 3 | 0.78 | g |
| 2-Methyl-5-(N-β-hydroxyethylamino)-phenol | 0.49 | g |
| Ethylene glycol monobutyl ether | 5 | g |
| Lauryl alcohol oxyethyleneated with 10.5 mols of ethylene oxide | 5 | g |
| 22° B strength ammonia solution | 10 | g |
| Water q.s.p. | 100 | g |
| The pH of this composition is equal to 11. | | |

70 g of hydrogen peroxide of 20 volumes strength are added at the time of use. When applied to bleached hair for 20 minutes at 20° C., this mixture imparts to the hair, after rinsing and shampooing, a light salmon-pink coloration.

EXAMPLE 38

The following dyeing composition is prepared:

| | | |
|---|---|---|
| Compound of Example 1 | 0.8 | g |
| Compound of Example 2 | 1 | g |
| 4-(N-Ethyl-N-carbamylmethylamino)-aniline | 0.1 | g |
| Meta-aminophenol | 1 | g |
| 6-Aminobenzomorpholine dihydrochloride | 0.035 | g |
| 2,6-Diaminohydroquinone dihydrochloride | 0.1 | g |
| 6-Hydroxybenzomorpholine | 0.51 | g |
| 2,6-Dimethyl-3-nitro-4-(N-β-hydroxyethylamino)-phenol | 0.2 | g |
| 2,4'-Diamino-4-hydroxy-5-methyldiphenylamine | 0.1 | g |
| Oleyl alcohol oxyethyleneated with 2 mols of ethylene oxide | 4.35 | g |

-continued

| | | |
|---|---|---|
| Oleyl alcohol oxyethyleneated with 4 mols of ethylene oxide | 8.7 | g |
| Propylene glycol | 8.7 | g |
| 22° B strength ammonia solution | 10 | g |
| Water q.s.p. | 100 | g |
| The pH of this composition is equal to 10. | | |

50 g of hydrogen peroxide of 20 volumes strength are added at the time of use. When applied to bleached hair for 20 minutes at ambient temperature, this mixture imparts to the hair, after rinsing and shampooing, a deep brown coloration.

EXAMPLE 39

The following dyeing composition is prepared:

| | | |
|---|---|---|
| Compound of Example 2 | 0.05 | g |
| Compound of Example 1 | 0.2 | g |
| Para-aminophenol | 0.42 | g |
| Resorcinol | 0.2 | g |
| 3-Nitro-4-(N-β-hydroxyethylamino)-phenol | 0.065 | g |
| Ammonium $C_{12}$, $C_{14}$-alkyl-sulphate (70% of $C_{12}$ and 30% of $C_{14}$) | 15 | g |
| Lauryl alcohol containing 10.5 mols of ethylene oxide | 5 | g |
| 22° B strength ammonia solution | 10 | g |
| Water q.s.p. | 100 | g |
| The pH of this composition is equal to 11.4. | | |

70 g of hydrogen peroxide of 20 volumes strength are added at the time of use. When applied to bleached hair for 15 minutes at 26° C., this mixture imparts to the hair, after rinsing and shampooing, a golden honey coloration.

EXAMPLE 40

The following dyeing composition is prepared:

| | | |
|---|---|---|
| Compound of Example 3 | 0.7 | g |
| Compound of Example 1 | 1 | g |
| Para-aminophenol | 0.32 | g |
| 4-Aminodiphenylamine | 0.23 | g |
| (2,4-Diamino)-phenoxyethanol dihydrochloride | 0.19 | g |
| Resorcinol | 0.34 | g |
| Meta-aminophenol | 0.35 | g |
| Ammonium $C_{12}$, $C_{14}$-alkyl-sulphate (70% of $C_{12}$ and 30% of $C_{14}$) | 15 | g |
| Lauryl alcohol containing 10.5 mols of ethylene oxide | 5 | g |
| 22° B strength ammonia solution | 10 | g |
| Water q.s.p. | 100 | g |
| The pH of this composition is equal to 10. | | |

80 g of hydrogen peroxide of 20 volumes strength are added at the time of use. When applied to bleached for 25 minutes at 25° C., this mixture imparts to the hair, after rinsing and shampooing, a smoke-grey coloration.

EXAMPLE 41

The following dyeing composition is prepared:

| | | |
|---|---|---|
| Compound of Example 2 | 2.79 | g |
| Ortho-aminophenol | 0.327 | g |
| Oleyl alcohol oxyethyleneated with 2 mols of ethylene oxide | 4.5 | g |
| Oleyl alcohol oxyethyleneated with 4 mols of ethylene oxide | 4.5 | g |
| Laurylamine oxyethyleneated with 12 mols of ethylene oxide | 4.5 | g |
| Diethanolamides of copra fatty acids | 9 | g |
| Propylene glycol | 3.6 | g |
| Ethylene glycol monobutyl ether | 8 | g |
| Ethanol | 5.4 | g |
| Aqueous sodium bisulphite solution (d = 1.32) | 1 | g |
| 22° B strength ammonia solution | 10 | g |
| Water q.s.p. | 100 | g |
| The pH of this composition is equal to 10.3. | | |

100 g of hydrogen peroxide of 20 volumes strength are added at the time of use. When applied at 95% strength to natural white hair for 20 minutes at 26° C., this mixture imparts to the hair, after rinsing and shampooing, a tin grey coloration.

A dyeing composition, which differs from the composition indicated above only in that ortho-aminophenol is absent, is applied under the same conditions to hair from the same batch; a slightly pinkish beige coloration is then obtained.

We claim:

1. A composition suitable for dyeing keratin fibres which comprises an aqueous solution containing at least one compound of the general formula:

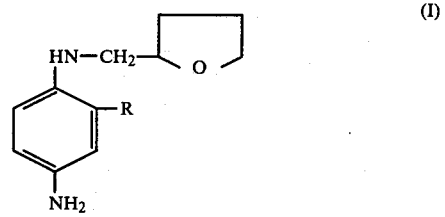

in which formula R is selected from the group consisting of a hydrogen atom, a chlorine atom and a methyl radical, or a salt thereof.

2. A composition according to claim 1 which is suitable for dyeing human hair.

3. A composition according to claim 1 in which R is selected from a chlorine atom and a methyl radical.

4. A composition according to claim 1 in which the salt is a hydrochloride, sulphate, phosphate or tartrate.

5. A composition according to claim 1 which contains from about 0.05% to about 6% by weight of compound of formula (I), based on the total weight of the composition.

6. A composition according to claim 1, which has a pH from about 8 to about 11.5.

7. A composition according to claim 1 which contains at least one other para or an ortho-phenylenediamine or ortho-or para-aminophenol.

8. A composition according to claim 1 which contains at least one coupler selected from the group consisting of meta-phenylenediamines, meta-diphenols, α-naphthol, meta-aminophenols, meta-acetylamino)-phenols, meta-ureidophenols, meta-(carbalkoxyamino)-phenols, 6-hydroxybenzomorpholine and pyrazolones.

9. A composition according to claim 8 which contains resorcinol.

10. A composition according to claim 9 in which R represents hydrogen.

11. A composition according to claim 8 which contains 2-methyl-5-(N-β-hydroxyethylamino)-phenol and/or meta-aminophenol.

12. A composition according to claim 8 which contains 2-methoxy-5-(carbethoxyamino)-phenol.

13. A composition according to claim 8 which contains (2,4-diamino)-phenoxyethanol and/or 6-aminobenzomorpholine.

14. A composition according to claim 13 in which R represents hydrogen.

15. A composition according to claim 1 which contains at least one leuco derivative of an indoaniline, indamine or indophenol, or a polyphenol, polyaminophenols, monoaminodiphenol or diaminodiphenol oxidative dyestuff.

16. A composition according to claim 15 which contains 4,4'-dihydroxy-2-amino-5-methyldiphenylamine and/or 2,4'-diamino-4-hydroxy-5-methyldiphenylamine.

17. A composition according to claim 1 in which contains at least one direct dyestuff.

18. A composition according to claim 17 in which the direct dyestuff is a nitrobenzene dyestuff.

19. A composition according to claim 18 which contains 3-nitro-4-(N-$\beta$-hydroxyethylamino)-phenol, 1-methoxy-3-nitro-6-(N-$\beta$-hydroxyethylamino)-benzene or 3-nitro-4-(N'-methylamino)-N-di-$\beta$-hydroxyethylaniline.

20. A composition according to claim 1 which contains at least one alkalising or acidifying agent, solvent, polymer, cationic treatment product, amide, thickener, surface-active agent, sunlight filter, optical brightener, antioxidant, sequestering agent or perfume.

* * * * *